(12) United States Patent
Liu (10) Patent No.: US 8,087,932 B2
(45) Date of Patent: Jan. 3, 2012

(54) CORRECTING THE POSITION OF TEETH IN DENTAL ARCH MODEL

(75) Inventor: Frank Zhenhuan Liu, San Carlos, CA (US)

(73) Assignee: Align Technology, Inc., San Jose, CA (US)

( * ) Notice: Subject to any disclaimer, the term of this patent is extended or adjusted under 35 U.S.C. 154(b) by 178 days.

(21) Appl. No.: 11/906,994

(22) Filed: Oct. 3, 2007

(65) Prior Publication Data

US 2008/0318179 A1 Dec. 25, 2008

Related U.S. Application Data

(60) Provisional application No. 60/849,411, filed on Oct. 3, 2006.

(51) Int. Cl.
*A61C 3/00* (2006.01)

(52) U.S. Cl. ......................................... 433/24; 382/128

(58) Field of Classification Search .................... 433/24, 433/213; 382/128
See application file for complete search history.

(56) References Cited

U.S. PATENT DOCUMENTS

| 6,488,499 B1 | 12/2002 | Miller |
| 6,761,560 B2 | 7/2004 | Miller |
| 7,037,108 B2 | 5/2006 | Chishti et al. |
| 2005/0048432 A1* | 3/2005 | Choi et al. ........................ 433/24 |
| 2006/0275731 A1* | 12/2006 | Wen et al. ........................ 433/24 |

* cited by examiner

*Primary Examiner* — Cris L Rodriguez
*Assistant Examiner* — Eric Rosen (57) ABSTRACT

A method of correcting a dental arch model so that it accurately reflects the current arrangement of a subject's teeth includes positioning a plurality of tooth models in a corrected arrangement using a representation of at least a portion of a subject's current dental arch (wherein the tooth models comprise models of the subject's teeth having fiduciary markers), and producing a base plate configured to hold the plurality of tooth models in the corrected arrangement. The representation of the current arrangement may be, for example, a physical impression of the subject's teeth, a 3D scan or one or more 2D scans of the subject's teeth.

10 Claims, 4 Drawing Sheets

CORRECTING THE POSITION OF TEETH IN DENTAL ARCH MODEL

The present application claims the benefit of U.S. Provisional Application Ser. No. 60/849,411, filed Oct. 3, 2006, which is incorporated herein by reference in its entirety.

BACKGROUND

This application generally relates to the field of dental care, and more particularly to dental arch models used in dental treatment.

In the course of a subject's (e.g., dental patient's) dental treatment, a dental arch model may be created to represent the arrangement of the subject's teeth. Errors may be introduced in a subject's dental arch model as the subject's teeth move. Teeth may move as the subject ages, or because of changes induced by treatment of the teeth (e.g., orthodontic treatment). Thus, it may be difficult to accurately reflect tooth position, even during treatment to correct the position of teeth. Overcorrection or undercorrection may occur (e.g., a tooth may move too far or too quickly).

Currently available methods of correcting a dental arch model are inadequate because they are either too time consuming or too expensive. Examples of mid-course correction methods are described in U.S. Pat. No. 6,488,499 and U.S. Pat. No. 6,761,560 to Miller, and U.S. Pat. No. 7,037,108 to Chishti et al., herein incorporated by reference in their entirety. Many of these methods require complex and expensive techniques for correcting a course of treatment used to realign or straighten teeth. For example, U.S. Pat. No. 6,488,499 and U.S. Pat. No. 6,761,560 require additional aligners to be designed and provided to bring a patient's teeth back into position, so that an original course of treatment can be resumed. These additional aligners add cost and time to the treatment.

Thus, there is a need for a method of updating and correcting the position of teeth in a dental arch model (e.g., a digital or virtual model, and/or an actual, physical dental arch model). The methods and systems describe herein address this need.

BRIEF SUMMARY OF THE INVENTION

Described herein are methods of correcting dental arch models so that they accurately reflect the current arrangement of a subject's teeth.

In one embodiment, a method of correcting a dental arch model so that it accurately reflects the current arrangement of a subject's teeth includes positioning a plurality of tooth models in a corrected arrangement using an impression of at least a portion of a subject's current dental arch (wherein the tooth models comprise models of the subject's teeth having fiduciary markers), and producing a base plate configured to hold the plurality of tooth models in the corrected arrangement.

Embodiments may include the steps of arranging a plurality of tooth models based on at least a portion of an impression of subject's current dental arch to form a corrected arrangement (wherein the tooth models comprise models of the subject's teeth having fiduciary markers), scanning the arrangement of the fiduciary markers on the tooth models in the corrected arrangement, updating the arrangement of digital tooth models in a digital model of the subject's dental arch based on the fiduciary markers, and producing a base plate configured to maintain the plurality of tooth models in the corrected arrangement based on the digital model of the dental arch.

Also, methods of correcting a digital dental arch model so that it accurately reflects the current arrangement of a subject's teeth are also described. These methods may include the steps of comparing a digital dental arch model with at least a region of a subject's current dental arch, and modifying the arrangement of teeth in the digital dental arch model to match the arrangement of teeth in the representation of the subjects' current dental arch.

Embodiments may include the steps of comparing a representation of a subject's current dental arch to a digital model of the subject's dental arch, and adjusting the position of the teeth in the digital model of the subject's dental arch based on the position of the teeth in the representation of the subject's current dental arch.

Embodiments may also include the steps of comparing a 2D image of a subject's current dental arch to a projected image of a digital model of the subject's dental arch, and adjusting the position of the teeth in the digital model to approximate the position of the teeth in the 2D image of the subject's current dental arch.

Similarly, embodiments may include the steps of comparing a 3D representation of a subject's current dental arch to a digital model of the subject's dental arch, and adjusting the position of the teeth in the digital model to approximate the position of the teeth in the 3D model of the subject's current dental arch.

These and other embodiments, features and advantages will become more apparent to those skilled in the art when taken with reference to the following more detailed description of the invention in conjunction with the accompanying drawings that are first briefly described.

DETAILED DESCRIPTION OF EMBODIMENTS

The following detailed description should be read with reference to the drawings. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention. The metes and bounds of the invention are defined by the claims that follow this description.

The general goal of the methods described herein is to make a model of a subject's dental arch correspond to the actual position of the subject's teeth, where the subject is undergoing treatment to adjust the position of their teeth within their dental arch. In particular, the treatment may be treatment with a series of dental aligners, such as described in international application PCT/US2005/039715 to Wen et al., filed Nov. 2, 2005, and international application PCT/US06/14124 to Wen et al., filed Mar. 3, 2006. International applications PCT/US2005/039715 and PCT/US06/14124 are hereby incorporated by reference in their entirety.

A. Terms Used Herein Include (Unless Defined Otherwise):

a. Correcting position (or arrangement)—the correct arrangement of teeth may reflect the patients actual teeth arrangement in their dental arch at some appropriate time during treatment. Thus, the model of the dental arch (a physical model or digital model) may be corrected from a predicted or target dental arch arrangement into the actual position as described herein. The position of teeth in the dental model may be based on pervious or anticipated position of teeth in an earlier dental arch model made from the subject's earlier tooth position. The methods described herein can generally be used to correct the entire model of the subject's dental arch or just a focused region (e.g., subset) of the subject's dental arch.

b. The model (dental arch model) can refer to either a digital or physical model (or both). Furthermore correcting the physical dental arch model may be used to correct a digital dental arch model, and correcting a digital dental arch model may be used to correct the physical dental arch model. For example, correcting the digital dental arch model may allow for the formation (e.g., by CNC drilling) of a new base plate so that individual tooth models with pins (or other fiduciary markers) can be placed into position in the new "corrected" base plate to give a corrected physical dental arch model. Likewise, a new physical arch model can be scanned to produce a new (corrected) digital dental arch model.

c. "Scan" can refer to either a whole scan or a partial scan of subject's teeth (dental arch).

d. "Impression" typically refers to an impression (e.g., based on a bite, or the use of a triple tray, etc.) of all the teeth or part of the subject's dental arch (e.g., showing tooth position). Thus, an impression may be a negative impression or a cast formed from an impression (e.g., either a positive or negative impression).

B. Making a Model of a Dental Arch

The method of making a dental arch model (a physical or digital model) is described in the PCT/US2005/039715 and PCT/US06/14124 references incorporated herein by reference, and as known in the art. Briefly, a dental impression of the subject's dental arch and/or images of the subject's dental arch are used to arrange accurate representation of the subject's teeth. For example, to form a physical model, a negative impression is used to case the subject's dental arch, and individual teeth models are marked with fiduciary marks (e.g., pins representing the roots). The positions of the fiduciary marks can be scanned to give the relationship between the marks and the teeth in the actual dental arch, and/or a base plate that mates with the marks (e.g., pins) can be fabricated either directly from the pins or from the digital model (e.g., by CNC manufacturing). The individual teeth (from the case) are then cut apart. These teeth models may be digitized (or scanned) and then the individual models of the teeth arranged into a digital model of the subject's dental arch. The physical tooth models can be aligned into the base plate (that receives the fiduciary marks (pins) on each tooth model) and holds the tooth models in a position that reflects the actual or a desired arrangement of the subject's teeth. These models (the digital model and the physical teeth models) may then be used to form a series of dental aligners by moving the teeth models by small increments towards a desired position, and then forming one or more dental aligners over the physical tooth models.

Errors can be introduced as teeth are moved using a method such as the one described above.

Typically most arch models are corrected by repeating the process described above to form a model of the entire dental arch, including fabricating the models of the teeth. This is expensive and time consuming.

One or more embodiments of the present invention compare a model of the dental arch to a representation of the actual dental arch position, move the teeth in the model to match the position of teeth in the representation (forming a corrected model), and check for errors in the corrected model. Below we describe three variations of this general method: a physical or "hardware" based approach, a 3D scan approach and a 2D scan approach.

1. Hardware Approach

In the hardware approach (see FIG. 1), a partial or complete impression of subject's teeth is provided (e.g., crown region only, etc.) and used to directly position individual tooth models in the current arrangement. The tooth models have fiduciary marks (e.g., pins). These fiduciary marks are then used to form a base plate for holding the teeth in the current position. The locations of the fiduciary marks can also be read and stored digitally to create a digital model of the current position of the teeth.

Thus, the impression is used as a template to position models of the teeth that were formed for this patient at the start of the treatment process. This prevents having to form new teeth models, since the shape of the teeth generally will not change, or will not change from the time the first physical tooth models are made.

Figure 1:
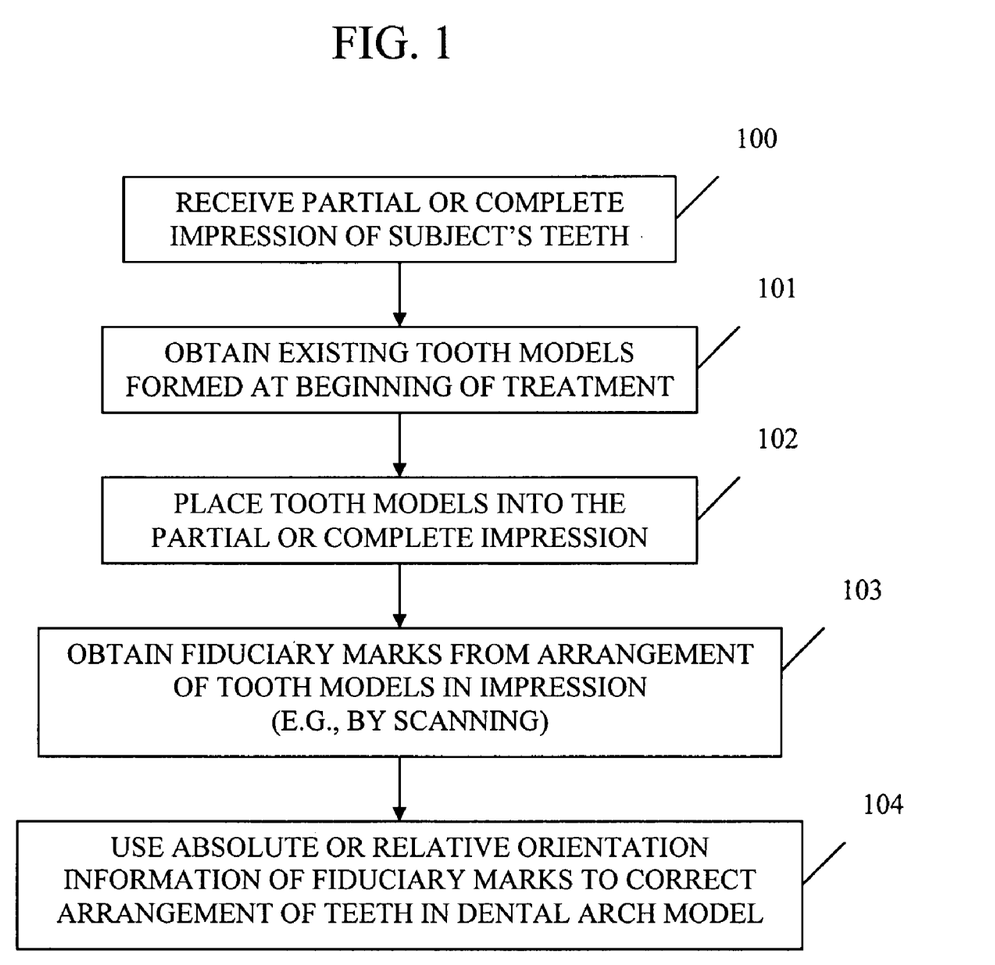
FIG. 1 illustrates a method for correcting teeth position in a dental arch model, using hardware in accordance with one or more embodiments of the invention.

An embodiment of the hardware approach is illustrated in the flow diagram of FIG. 1. The dentist may typically provide a complete negative impression, or a partial impression of the subject's teeth (100). In some variations a wax bite may be sufficient. In other variations, it may be desirable to use a cast dental impression. To facilitate the collection of fiduciary marks from the impression, the individual tooth models formed at the beginning of the treatment may be provided (101). The corresponding tooth models may be positioned (102) within the impression (e.g., with respective pins facing away from the impression).

After positioning the tooth models in the provided ("correct") impression of the dental arch (or portion of the dental arch), the fiduciary marks (referred to herein as pins, although any appropriate marks may be used) may be scanned (103). The orientation information gathered from the scanning process is used to correct the arrangement of teeth in the dental arch model (104).

Figure 2:
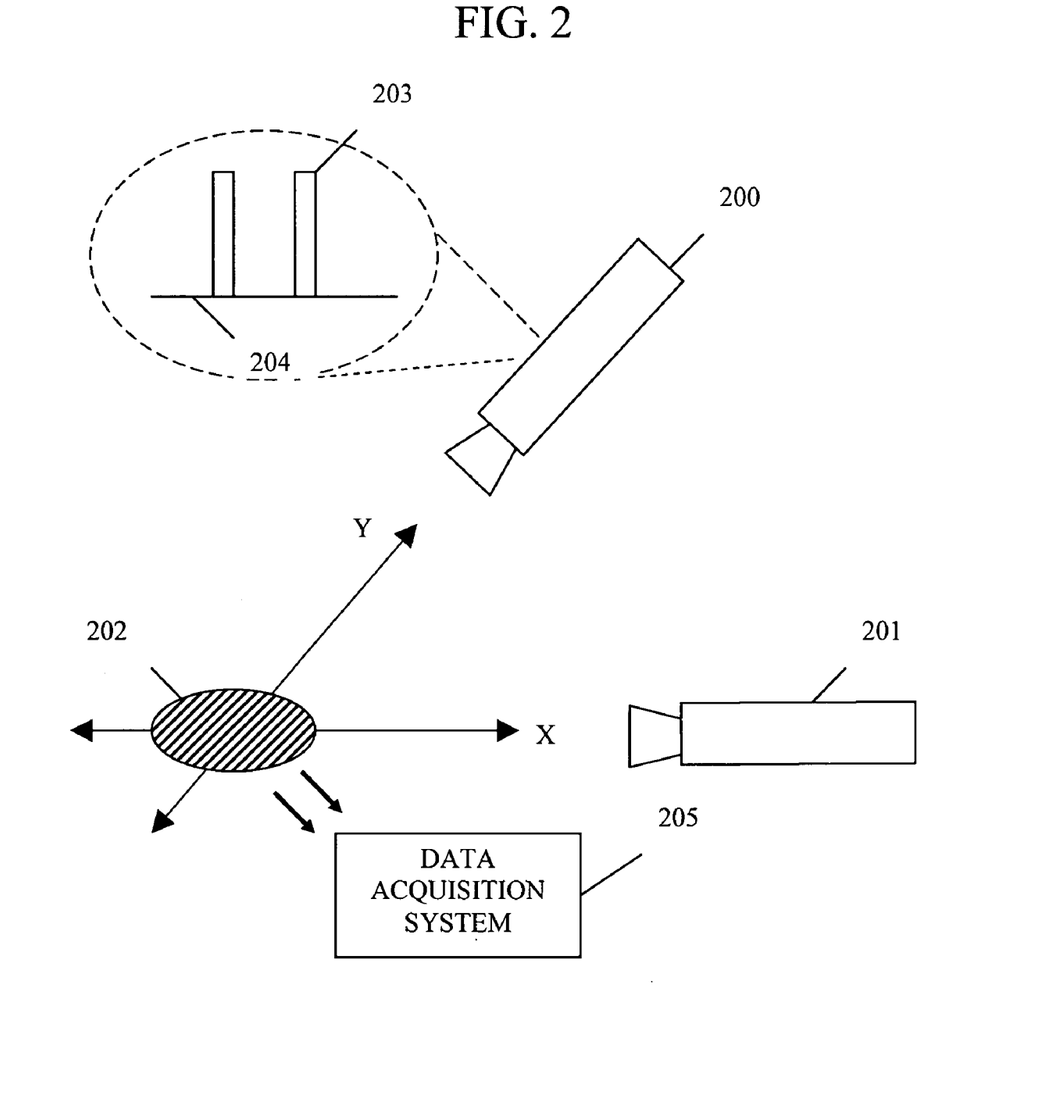
FIG. 2 illustrates a hardware set-up for implementing mid-course correction, in accordance with an embodiment of the invention.

FIG. 2 shows one example of a set-up for performing the scanning process (e.g., including cameras (200, 201), a rotary table and X-Y stage (202), and a data acquisition system (205), etc.) to correct the digital model. Using this setup, each tooth model may be measured, one by one. For example, the impression may be rotated and transitioned (e.g., on rotary table and X-Y stage 202) so that the pins 203 of the tooth model of interest are perpendicular to the camera axis (the pegged surface 204 is parallel to the camera axis). The image in the camera appears as represented by the encircled camera view in FIG. 2. This process is done for both cameras. With the rotation angles and the transition values, the tooth/pin coordinates may be calculated.

2. 3D Scan Approach

Figure 3:
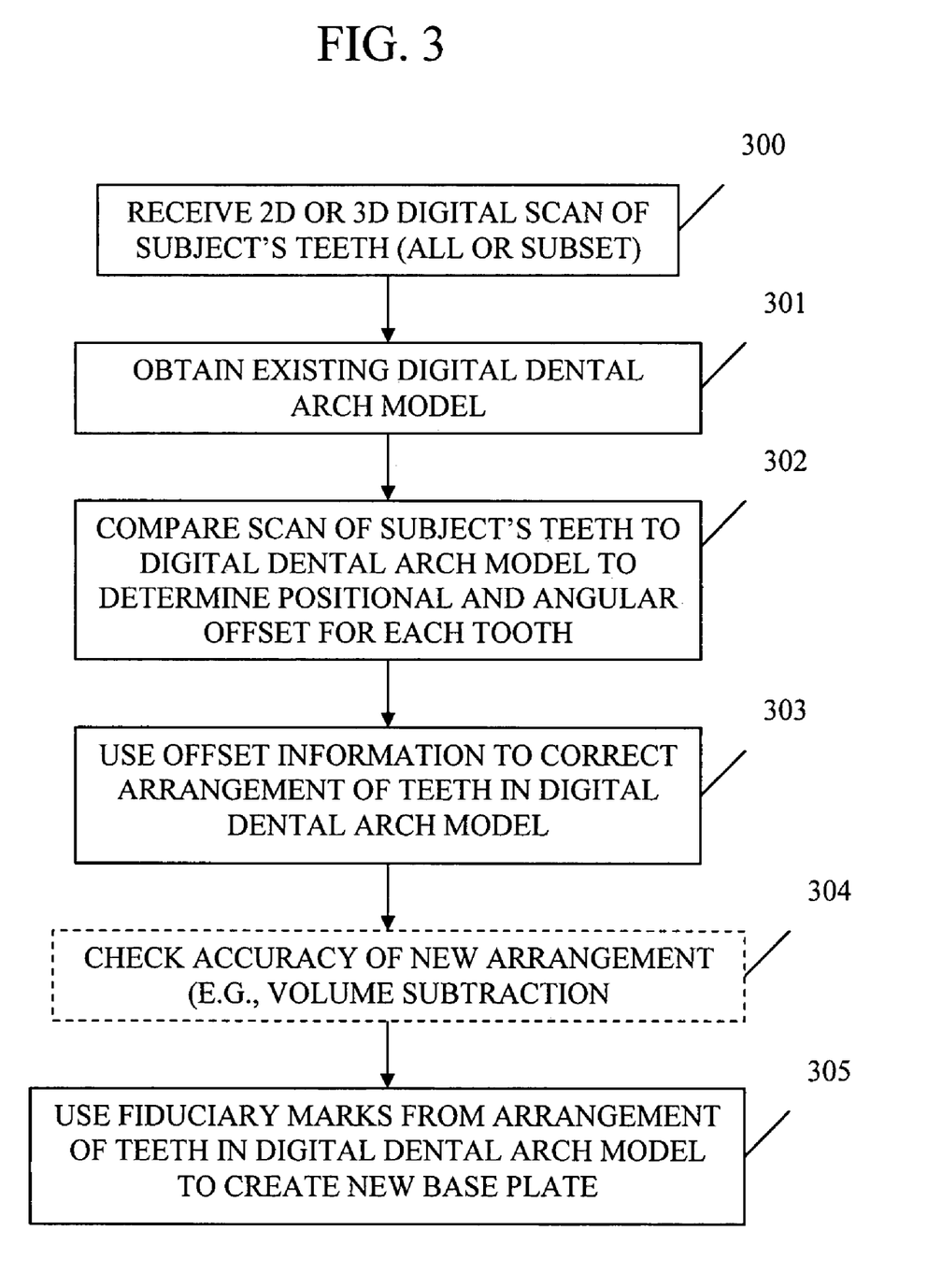
FIG. 3 illustrates a method for correcting teeth position in a dental arch model, using software in accordance with one or more embodiments of the invention.

Instead of providing an impression or cast of the subject's teeth (particularly an ill-fitting region), the dentist may provide a 3D scan of the subject's actual (e.g., current) dental arch or a sub-region of the dental arch, as shown in block 300 of FIG. 3. For example, this may be provided as a direct (digital) scan of the subject's teeth, or a series of images (including digital images) of the subject's teeth. It may also be a scan of a dental impression, including a 3D model (or a series of images) of a negative impression of the subject's teeth. The provided scan may be converted to a representation of the position (e.g., absolute or relative to other teeth in the subject's dental arch) for comparison with a digital model of the subject's teeth.

In this method, the arrangement of the subject's teeth in the digital dental arch model (see 301) may be compared to the 3D digital model of teeth provided (302). The difference in teeth position between the actual arrangement and the modeled arrangement of the subject's dental arch may be calculated by determining the difference in position of each tooth within the dental arch between the two, and calculating the offset in each tooth of the arch. Finally, the tooth model may be translated this offset amount (and direction) using the fiduciary markers (pins)(see 303).

The method of comparison of the 3D surfaces may be done by surface matching, as is known in the art. In some variations, the comparison of 3D surfaces between the actual and the modeled teeth may be done by comparing a 2D projection of one or the other 3D model (e.g., the tooth model or the actual tooth arrangement) with a 2D projection the other 3D model as it is rotated. The amount of rotation to get a match may be used to determine the offset. In another variation, the difference in position of individual teeth between the actual and virtual models may be determined by setting a threshold for error, and simulating motion of each tooth in dental arch from the position of the tooth model to the actual position of the dental arch model. The virtual teeth of the dental arch model many then be moved to reflect the new (actual current position) in the digital arch model. This may result in a new (and accurate) digital arch model that also includes the fiduciary marks (e.g., pins), so that a corrected physical arch model can be made by making a new base plate (305), since the pin positions on the virtual teeth now reflect the current pin position in the actual arrangement of the teeth.

The accuracy of the new arrangement may be checked by again comparing the position of the tooth model to the current actual dental arch arrangement (304). In this checking comparison, a different comparison method may be used to save time. For example, volume subtraction may be used. Using volume subtraction, the overlapping volumes of the actual dental arch and the corrected (modeled) dental arch are subtracted. The difference in the two volumes (the minimum non-overlapping region) is the error between the two. A threshold error may be set (e.g., less than 5%, less than 1%, less than 0.5%, less than 0.1%, less than 0.05%, less than 0.01%, or some intermediate value), and error exceeding this threshold results in a "failure" of the correction technique. In this case, the correction technique is not used, and a completely new model of the teeth may be made starting from the actual "current" position (e.g., making new tooth models, etc.).

3. 2D Image or Scan Approach

In this embodiment, one (or preferably more) 2D images of the current dental arch or a portion of the current dental arch (e.g., picture of ill-fitting region) are provided (see 300 in FIG. 3) and can be used to correct the position of the subject's teeth. For example, the dentist or practitioner may provide images (including x-rays, photographs, etc.) of the subject's teeth. The digital model of the subject's teeth (the model to be corrected, 301) may then be compared to these images (302), and the difference between the actual tooth position shown in the images (or scans) and the digital model may be calculated. In some variations, the difference is not expressly calculated, but the digital models of the individual teeth (including the associated fiduciary marks) are moved (303).

For example, the digital model can be compared to the 2D picture (scan) of the subject's current actual teeth position by making a 2D projection of the teeth arranged in the digital model, as taken from the same perspective shown in the provided 2D image(s). The digital model can then be modified until the projections of the teeth in the digital model match the images of the current dental arch model. "Matching" can be determined by any appropriate method. For example, a match may be done manually (by having a technician "eyeball" the two, and move the teeth of the digital model until it "looks like" the picture shown), or automatically. In one automatic variation, the digital model is used to make a projection of the teeth in approximately the same orientation as the image provided (e.g., the same perspective of the teeth), and the projected tooth profile from the digital model (a "virtual image") is subtracted from the image provided of the actual position of the corresponding teeth. Using the digital model, the teeth position are iteratively examined (e.g., through each projection of the teeth), and edge matching can be used to subtract the difference between individual tooth in the actual position of the dental arch with the corresponding teeth positioned in the 2D image projection from the model. Since each tooth in the digital model may be individually moved, it can be moved until the correct 2D image (or two or more 2D images) matches the position for each tooth. Once the amount that each tooth needs to be moved to match the image(s) provided, the individual teeth in the model may be moved to produce the corrected digital dental arch model.

As mentioned above, from the corrected digital dental arch model, a new physical arch model may be made by, for example, making a new base plate to fit the fiduciary markers that corresponds to the markers in the physical tooth models (305).

Also as described above for the 3D scanning technique, the accuracy of the position of the corrected dental arch tooth models may be checked (304). For example, surface area subtraction may be done to determine if the difference between the corrected model and the image(s) provided falls within an acceptable range. Thus, 2D projections from the digital dental arch model may be generated in the same perspective as the provided image(s), and the edges of the surfaces compared. Differences in the two surfaces (e.g., where they do not align) may be determined, and compared to a threshold value. As mentioned above, a threshold error may be set (e.g., less than 5%, less than 1%, less than 0.5%, less than 0.1%, less than 0.05%, less than 0.01%, or some intermediate value), and an error exceeding this threshold results in a "failure" of the correction technique. In this case, the correction technique is not used, and a completely new model of the teeth may be made starting from the actual "current" position (e.g., making new tooth models, etc.). (See blocks 410-413 of FIG. 4)

C. Applications

Figure 4:
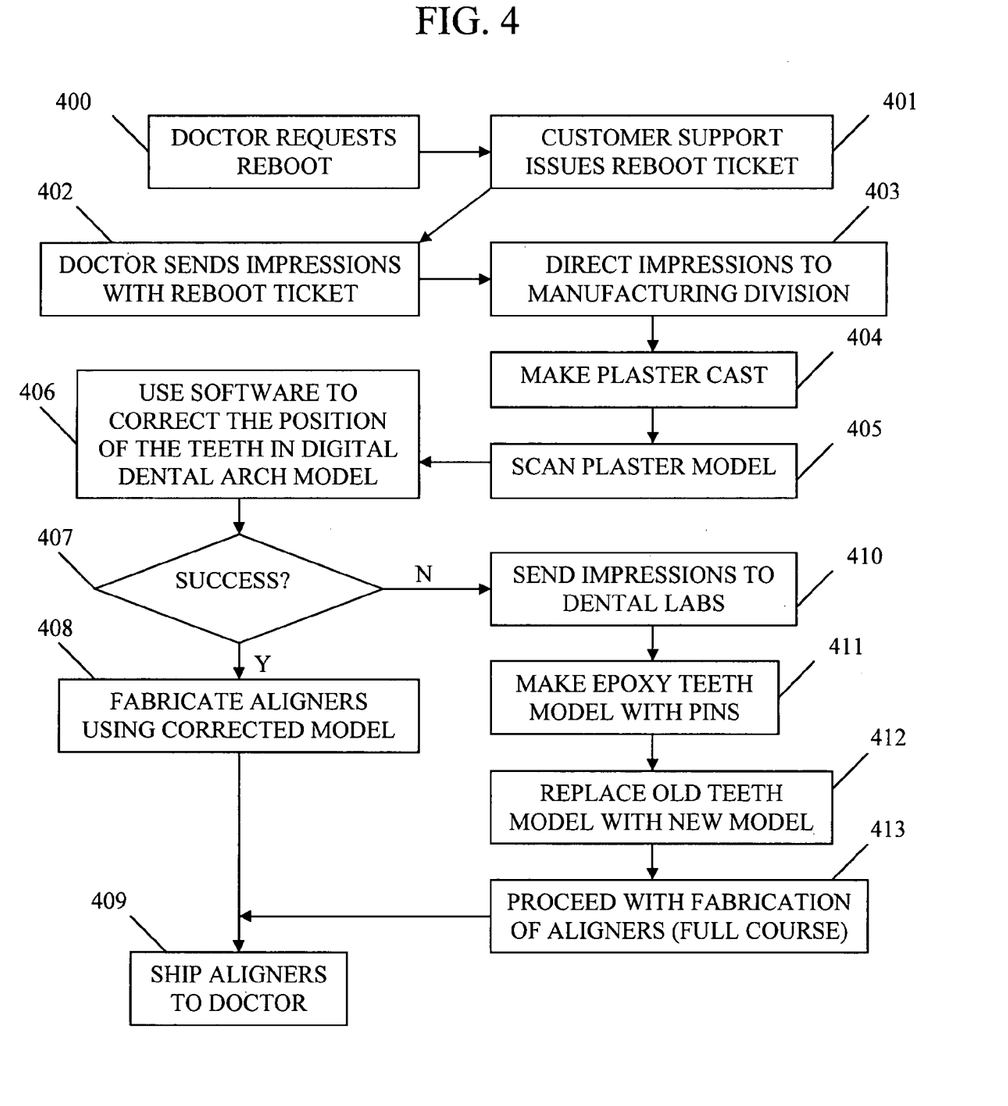
FIG. 4 illustrates an example application in which an embodiment of the invention may be implemented.

As mentioned, the methods described herein may be applied to mid-course correction of a treatment for correcting dental arch alignment. FIG. 4 illustrates (in flow-chart form) how such a method may be applied to that process of providing dental aligners to treat teeth. In this example, a 3D scan approach is used. A dental impression is provided by the clinician (402), and a plaster cast of the current dental alignment is made and scanned (404, 405), and compared to the arrangement of the teeth in the digital model. Corrections to the digital model are made (406), and the accuracy of the correction is checked (the "success" of the correction), as shown (407).

It would also be possible to use either the hardware approach or the 2D scan approach with the process shown in FIG. 4. For example, since a dental impression of the actual representation of the teeth is provided, the hardware approach would entail placing the individual tooth models (having fiduciary marks) into the negative impression and scanning the resulting pin positions and/or making a new base plate, as described above. Comparison may then be made with the dental impression or a positive mold made from the dental impression.

The 2D approach may be used with the process in FIG. 4 (or a similar process). For example, the 2D approach may be used by making a positive cast of the teeth from the negative impression, and taking images of the resulting cast for comparison to projections of the digital model as described above.

In FIG. 4, the updating or correction of the physical or digital model is triggered by a practitioner (shown as a doctor in FIG. 4) requesting "re-boot" or correction (400). For example, the doctor or subject wearing the aligners may notice that the aligner (or a portion of the aligner) does not fit properly. In some variations, this comparison may occur automatically. For example, the practitioner may provide new images, models, impressions and/or wax bites of the subject's teeth each time the subject receives a new aligner, or otherwise receives a check up (e.g., an in-office checkup). These images, models, impressions or the like may then be sent to the aligner manufacturer/supplier (403) where a comparison (the "reboot" process described above) can be performed. Aligners may be fabricated based on the corrected model and shipped to the requesting doctor (408, 409).

Thus the method of correcting a dental arch model so that it accurately reflects the current arrangement of a subject's teeth may be automatically performed even when not triggered by an ill-fitting device. This automatic rebooting may benefit the user, since small divergences between the modeled dental arch in the physical or digital dental arch and the actual position of the subject's teeth may not be noticed immediately, but may gradually erode patient comfort and the effectiveness of the appliance. Automatic correction may prevent this.

This invention has been described and specific examples of the invention have been portrayed. While the invention has been described in terms of particular embodiments and illustrative figures, those of ordinary skill in the art will recognize that the invention is not limited to the embodiments or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of correcting a digital dental arch model to accurately reflect a current arrangement of teeth of a subject, the method comprising:
    positioning a plurality of individual physical tooth models of the subject's teeth within an impression of a current dental arch of the subject, wherein the plurality of individual physical tooth models comprises a first set of fiduciary marks in a first positional arrangement, the positioning comprising:
        placing the plurality of individual physical tooth models within the impression such that the first set of fiduciary marks faces away from the impression;
        scanning the plurality of individual physical tooth models that is positioned in the impression, including the first set of fiduciary marks, to achieve a first representation of the current dental arch of the subject;
    comparing the first representation of the current dental arch of the subject with a digital model of at least two teeth of a dental arch of the subject comprising a second set of fiduciary marks in a second positional arrangement, the second set of fiduciary marks being positioned on teeth within the digital model of at least two teeth of the dental arch of the subject, the digital model of at least two teeth of the dental arch of the subject being a digital model of at least two teeth of the dental arch of the subject before a latest treatment that resulted in the current dental arch of the subject, wherein the comparing the first representation of the current dental arch of the subject with the digital model of at least two teeth of the dental arch of the subject comprises:
        comparing the first positional arrangement of the first set of fiduciary marks, including fiduciary marks on at least two teeth in the first representation of the current dental arch of the subject, with the second positional arrangement of the second set of fiduciary marks;
    based on the comparing of the first representation of the current dental arch of the subject with the digital model of at least two teeth of the dental arch of the subject, adjusting a position of at least one tooth of the teeth in the digital model of at least two teeth of the dental arch of the subject to achieve an adjusted digital dental arch model that comprises an adjusted positional arrangement of the second set of fiduciary marks, wherein the adjusted positional arrangement of the second set of fiduciary marks on the teeth in the adjusted digital dental arch model reflect the positions relative to each other of the first set of fiduciary marks in the first representation of the current dental arch of the subject, and wherein the adjusted digital dental arch model is a second representation of the current dental arch of the subject; and
    producing a base plate based on the adjusted digital dental arch model, the base plate being configured for receiving the individual physical tooth models of the teeth of the subject such that the first set of fiduciary marks on the individual physical tooth models is arranged in a third positional arrangement, wherein the third positional arrangement of the fiduciary marks on the individual physical tooth models corresponds with the adjusted positional arrangement of the second set of fiduciary marks on the teeth in the adjusted digital arch model.

2. The method of claim 1, further comprising confirming an accuracy of the adjusted digital dental arch model.

3. The method of claim 1, wherein the first representation of the subject's current dental arch comprises a 3D representation of the current dental arch of the subject.

4. The method of claim 1, wherein the first representation of the subject's current dental arch comprises a 2D image of the current dental arch of the subject.

5. A method of correcting a digital dental arch model so that it accurately reflects a current arrangement of teeth of a subject, the method comprising:
positioning a plurality of individual physical tooth models of the subject's teeth within an impression of a current dental arch of the subject, wherein the plurality of individual physical tooth models comprises a first set of fiduciary marks in a first positional arrangement, the positioning comprising:
placing the plurality of individual physical tooth models within the impression such that the first set of fiduciary marks faces away from the impression;
scanning the plurality of individual physical tooth models that is positioned in the impression, including the first set of fiduciary marks, to achieve a first representation of the current dental arch of the subject, the first representation being a 2D image of the current dental arch of the subject;
comparing the 2D image of the current dental arch of the subject with a projected image of a digital model of at least two teeth of a dental arch of the subject comprising a second set of fiduciary marks in a second positional arrangement, the second set of fiduciary marks being positioned on teeth within the digital model of at least two teeth of the dental arch of the subject, the digital model of at least two teeth of the dental arch of the subject being a digital model of at least two teeth of the dental arch of the subject before a latest treatment that resulted in the current dental arch of the subject, the 2D image being the first representation of the current dental arch of the subject, wherein the comparing the 2D image of the current dental arch of the subject with the digital model of at least two teeth of the dental arch of the subject comprises:
comparing the first positional arrangement of the first set of fiduciary marks, including fiduciary marks on at least two teeth in the first representation of the current dental arch of the subject, with the second positional arrangement of the second set of fiduciary marks;
based on the comparing of the 2D image of the current dental arch of the subject with the digital model of at least two teeth of the dental arch of the subject, adjusting a position of at least one tooth in the digital model of at least two teeth of the dental arch of the subject to approximate a position of the teeth in the 2D image of the current dental arch of the subject to achieve an adjusted digital dental arch model that comprises an adjusted positional arrangement of the second set of fiduciary marks, wherein the adjusting the position of the at least one tooth in the digital model comprises:
calculating a difference between edges of the 2D image and edges of the projected image of the digital model of the current dental arch of the subject, wherein the adjusted positional arrangement of the second set of fiduciary marks on the teeth in the adjusted digital dental arch model reflect the positions relative to each other of the first set of fiduciary marks in the first representation of the current dental arch of the subject, and wherein the adjusted digital dental arch model is a second representation of the current dental arch of the subject; and
producing a base plate based on the adjusted digital dental arch model, the base plate being configured for receiving the individual physical tooth models of the teeth of the subject such that the first set of fiduciary marks on the individual physical tooth models is arranged in a third positional arrangement, wherein the third positional arrangement of the fiduciary marks on the individual physical tooth models corresponds with the adjusted positional arrangement of the second set of fiduciary marks on the teeth in the adjusted digital arch model.

6. The method of claim 5, wherein the adjusting the position of the at least one tooth in the digital model comprises manually adjusting the position of the at least one tooth.

7. The method of claim 5, further comprising confirming an accuracy of the adjusted digital dental arch model.

8. A method of correcting a digital dental arch model to accurately reflect a current arrangement of teeth of a subject, the method comprising:
positioning a plurality of individual physical tooth models of the subject's teeth within an impression of a current dental arch of the subject, wherein the plurality of individual physical tooth models comprises a first set of fiduciary marks in a first positional arrangement, the positioning comprising:
placing the plurality of individual physical tooth models within the impression such that the first set of fiduciary marks faces away from the impression;
scanning the plurality of individual physical tooth models that is positioned in the impression, including the first set of fiduciary marks, to achieve a first representation of the current dental arch of the subject, the first representation being a 3D image of the current dental arch of the subject;
comparing the 3D image of the current dental arch of the subject with a digital model of at least two teeth of a dental arch of the subject comprising a second set of fiduciary marks in a second positional arrangement, the second set of fiduciary marks being positioned on teeth within the digital model of at least two teeth of the dental arch of the subject, the digital model of at least two teeth of the dental arch of the subject being a digital model of at least two teeth of the dental arch of the subject before a latest treatment that resulted in the current dental arch of the subject, the 3D image being the first representation of the current dental arch of the subject, wherein the comparing the 3D image of the current dental arch of the subject with the digital model of at least two teeth of the dental arch of the subject comprises:
comparing the first positional arrangement of the first set of fiduciary marks, including fiduciary marks on at least two teeth in the first representation of the current dental arch of the subject, with the second positional arrangement of the second set of fiduciary marks;
based on the comparing of the 3D image of the current dental arch of the subject with the digital model of at least two teeth of the dental arch of the subject, adjusting a position of at least one tooth in the digital model of the dental arch of the subject to approximate a position of the teeth in the 3D image of the current dental arch of the subject to achieve an adjusted digital dental arch model that comprises an adjusted positional arrangement of the second set of fiduciary marks, wherein the adjusting the position of the at least one tooth in the digital model comprises:
calculating a difference between the 3D image of the current dental arch of the subject and the digital model of at least two teeth of the dental arch of the subject, wherein the adjusted positional arrangement of the second set of fiduciary marks on the teeth in the adjusted digital arch model reflect the positions relative to each other of the first representation of the current dental arch of the subject, and wherein the adjusted digital dental arch model is a second representation of the current dental arch of the subject; and producing a base plate based on the adjusted digital dental arch model, the base plate being configured for receiving the individual physical tooth models of the teeth of the subject such that the first set of fiduciary marks on the individual physical tooth models is arranged in a third positional arrangement, wherein the third positional arrangement of the fiduciary marks on the individual physical tooth models correspond with the adjusted positional arrangement of the second set of fiduciary marks on the teeth in the adjusted digital dental arch model.

9. The method of claim 8, wherein the adjusting the position of the at least one tooth in the digital model comprises manually adjusting the position of the at least one tooth.

10. The method of claim 8, further comprising confirming an accuracy of the adjusted digital dental arch model.

* * * * *

UNITED STATES PATENT AND TRADEMARK OFFICE
CERTIFICATE OF CORRECTION

PATENT NO. : 8,087,932 B2  
APPLICATION NO. : 11/906994  
DATED : January 3, 2012  
INVENTOR(S) : Frank Zhenhuan Liu Page 1 of 1

It is certified that error appears in the above-identified patent and that said Letters Patent is hereby corrected as shown below:

Col. 12, Claim 9: Delete "The method of claim 8, wherein the adjusting the position of the at least one tooth in the digital model comprises manually adjusting the position of the at least one tooth."

and replace with: "The method of claim 8, wherein the adjusting the position of at least one tooth in the digital model comprises manually adjusting the position of the teeth."

Signed and Sealed this
Twenty-eighth Day of February, 2012

David J. Kappos
*Director of the United States Patent and Trademark Office*

UNITED STATES PATENT AND TRADEMARK OFFICE
CERTIFICATE OF CORRECTION

PATENT NO. : 8,087,932 B2  Page 1 of 1
APPLICATION NO. : 11/906994
DATED : January 3, 2012
INVENTOR(S) : Frank Zhenhuan Liu

It is certified that error appears in the above-identified patent and that said Letters Patent is hereby corrected as shown below:

Col. 12, lines 5-7, Claim 9: Delete "The method of claim 8, wherein the adjusting the position of the at least one tooth in the digital model comprises manually adjusting the position of the at least one tooth."

and replace with: "The method of claim 8, wherein the adjusting the position of at least one tooth in the digital model comprises manually adjusting the position of the teeth."

This certificate supersedes the Certificate of Correction issued February 28, 2012.

Signed and Sealed this
Twenty-seventh Day of March, 2012

David J. Kappos
*Director of the United States Patent and Trademark Office*